(12) United States Patent
Tanaka et al.

(10) Patent No.: US 8,318,990 B2
(45) Date of Patent: Nov. 27, 2012

(54) PROCESS OF PRODUCING ALCOHOL

(75) Inventors: Yoshiyuki Tanaka, Kurashiki (JP);
Masaru Utsunomiya, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 12/808,586

(22) PCT Filed: Dec. 9, 2008

(86) PCT No.: PCT/JP2008/072350
§ 371 (c)(1),
(2), (4) Date: Jun. 16, 2010

(87) PCT Pub. No.: WO2009/081727
PCT Pub. Date: Jul. 2, 2009

(65) Prior Publication Data
US 2010/0298613 A1    Nov. 25, 2010

(30) Foreign Application Priority Data
Dec. 20, 2007  (JP) ................... 2007-329066

(51) Int. Cl.
*C07C 27/00* (2006.01)
(52) U.S. Cl. ........ 568/905; 568/300; 568/700; 568/840; 568/888; 568/890
(58) Field of Classification Search .................. None
See application file for complete search history.

(56) References Cited

U.S. PATENT DOCUMENTS 3,479,412 A * 11/1969 Conti et al. .................. 568/905
3,862,994 A *  1/1975 Yates ........................... 568/905

OTHER PUBLICATIONS

Burk, L. Patrick et al., "The Rhodium-Promoted Guerbet Reaction Part I. Higher Alcohols From Lower Alcohols", Journal of Molecular Catalysis, vol. 33, pp. 1-14, (1985).
Tsuchida, Toshiyuki et al., "Hap Shokubai ni yoru Ethanol kara no Butanol Gosei", vol. 49, No. 3, pp. 238 to 243, (Apr. 10, 2007).
Ueda, Wataru et al., "A Low-presure Guerbet Reaction over Magnesium Oxide Catalyst", J., Chem., Society Communications, pp. 1558-1559, (1990).
Matsu-Ura, Toyomi et al., "Guerbet Reaction of Primary Alcohols Leading to β-Alkylated Dimer Alcohols Catalyzed by Iridium Complexes", Journal of Organic Chemistry, vol. 71, No. 21, pp. 8306-8308, (2006).
Carlini, Carlo et al., "Selective synthesis of 2-ethyl-1-hexanol from *n*-butanol through the Guerbet reaction by using bifuntional catalysts based on copper or palladium precursors and sodium butoxide", Journal of Molecular Catalysis A: Chemical, vol. 212, pp. 65-70, (2004).
Office Action dated Aug. 15, 2012, issued in corresponding Chinese patent application No. 200880115670.0 w/English translation.
G. Gregorio et al., "Condensation of Alcohols Catalysed by Tertiary Phosphine Transition Metal Complexes"—Journal of Organometallic Chemistry, vol. 37, No. 2, pp. 385-387, Apr. 16, 1972.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

A subject for the invention is to provide a process of producing a dimeric alcohol in high yield with high selectivity by the Guerbet reaction conducted using an alcohol having 4 or less carbon atoms as a starting material in the presence of a complex including a transition metal and of a base. The invention relates to a process of producing an alcohol which includes dimerizing a starting-material alcohol having 4 or less carbon atoms in an environment having a partial hydrogen pressure of 0.1 MPa or higher.

11 Claims, 1 Drawing Sheet

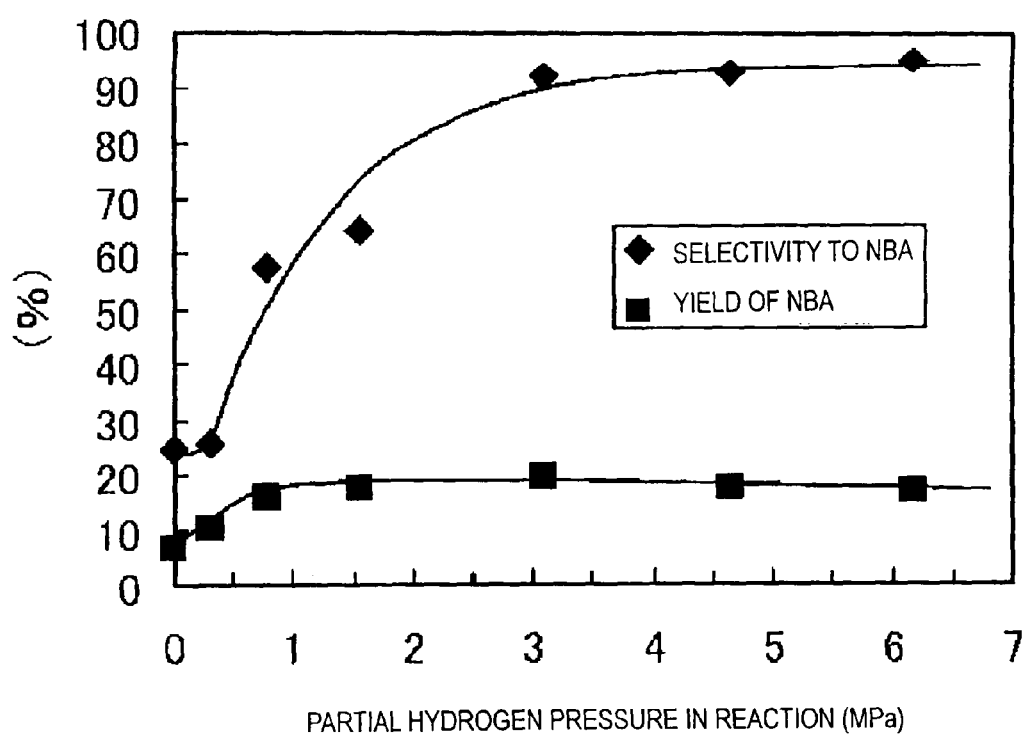

US 8,318,990 B2

PROCESS OF PRODUCING ALCOHOL

TECHNICAL FIELD

The present invention relates to a process of producing an alcohol by dimerizing a starting-material alcohol having 4 or less carbon atoms.

BACKGROUND ART

The Guerbet reaction is an important organic synthesis reaction as a process of producing a dimeric alcohol by dimerizing a starting-material alcohol. The mechanism of this reaction is thought to be as shown in the following reaction scheme 1. Namely, the reaction is thought to proceed on the basis of a combination of three reactions, i.e., a reaction in which a starting-material alcohol is caused to undergo a hydrogen abstraction reaction (hydrogen transfer reaction) using a basic compound and a complex of a transition metal with a phosphine compound to thereby yield the corresponding aldehyde intermediate, a reaction in which the aldehyde intermediate is dimerized by an aldol condensation reaction into an α,β-unsaturated aldehyde intermediate, and a reaction in which the α,β-unsaturated aldehyde intermediate undergoes a hydrogenation reaction (hydrogen transfer reaction) and thereby becomes a dimeric alcohol (non-patent document 1 and non-patent document 2).

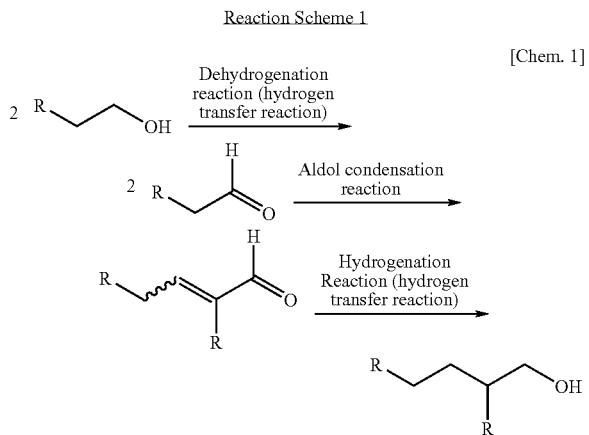

Reaction Scheme 1
[Chem. 1]

A process of dimeric-alcohol production based on the reaction mechanism has been applied to higher-alcohol production in which starting-material alcohols having 6 or more carbon atoms are used to obtain dimeric alcohols having 12 or more carbon atoms. These higher alcohols are used mainly as raw materials for cosmetics, emulsifying agents, etc.

However, there has been no case in which that reaction mechanism is applied to a starting-material alcohol having 4 or less carbon atoms. For example, there has been no case in which the starting-material alcohol is ethanol, which has 2 carbon atoms, and n-butanol is produced as a dimeric alcohol therefrom. This is because the yield of the n-butanol obtained and the selectivity to n-butanol are low and the reaction is not industrially advantageous. There has been a desire for a process of n-butanol production in which n-butanol is produced in high yield with high selectivity using a smaller amount of a catalyst.

Non-Patent Document 1: *J. Mol. Catal. A: Chem.*, 2004, 212, p. 65
Non-Patent Document 2: *J. Org. Chem.*, 2006, 71, p. 8306

DISCLOSURE OF THE INVENTION

Problem that the Invention is to Solve

In view of the problem described above, an object of the invention is to provide a process in which an alcohol having 4 or less carbon atoms is subjected as a starting material to the Guerbet reaction in the presence of a complex including a transition metal and of a base to produce a dimeric alcohol in high yield with high selectivity.

Means for Solving the Problems

The present inventors diligently made investigations in order to overcome the problem. As a result, they have found that the problem can be eliminated by reacting a starting material in pressurized hydrogen in the presence of a complex including one or more transition metals and of a base. The invention has been thus completed. Namely, essential points of the invention reside in the following [1] to [8].

[1] A process of producing an alcohol which comprises dimerizing a starting-material alcohol having 4 or less carbon atoms in an environment having a partial hydrogen pressure of 0.1 MPa or higher.

[2] The process of alcohol production according to [1], characterized by conducting the dimerization in the presence of a complex comprising one or more transition metals and of a base.

[3] The process of alcohol production according to [1] or [2], characterized in that the partial hydrogen pressure is 0.5-20 MPa.

[4] The process of alcohol production according to any one of [1] to [3], characterized in that the complex has a ligand derived from a phosphine compound.

[5] The process of alcohol production according to [4], characterized in that the phosphine compound is a triarylphosphine.

[6] The process of alcohol production according to any one of [1] to [4], characterized in that the transition metals are transition metals in Group 8 to Group 10.

[7] The process of alcohol production according to [6], characterized in that the transition metals in Group 8 to Group 10 are selected from the group consisting of ruthenium, rhodium, iridium, nickel, palladium, and platinum.

[8] The process of alcohol production according to any one of [1] to [7], characterized in that the starting-material alcohol having 4 or less carbon atoms is ethanol.

EFFECT OF THE INVENTION

According to the invention, n-butanol can be highly efficiently produced as a dimeric alcohol with high selectivity through a reaction in which ethanol as a starting material is dimerized in the presence of a base and a transition metal complex.

BRIEF DESCRIPTION OF THE DRAWING

FIG. 1 is graphs showing changes in the yield of n-butanol and the selectivity to n-butanol with changing partial hydrogen pressure during reaction, the graphs having been drawn using the numerical values given in Table 1.

BEST MODE FOR CARRYING OUT THE INVENTION

The following explanations on constituent elements are for embodiments (typical embodiments) of the invention, and the invention should not be construed as being limited to the embodiments. Details thereof will be explained below.

An embodiment of the invention is explained in which a complex including one or more transition metals in Group 8 to Group 10 and a base are used to produce n-butanol by the dimerization reaction of starting-material ethanol in an environment having a partial hydrogen pressure of 0.1 MPa or higher.

According to that embodiment of the process of the invention, in which n-butanol is produced by the dimerization reaction of starting-material ethanol, n-butanol can be obtained with high selectivity. The reason for this is presumed to be as follows, although it has not been entirely elucidated. Namely, it is thought that the crotonaldehyde intermediate which generated in the second stage according to the reaction mechanism (reaction scheme 1), which is chemically relatively unstable, was smoothly hydrogenated due to the effect of pressurized hydrogen without disappearing through a decomposition reaction and thereby rapidly changed into the stable form of n-butanol.

It is known that in the conventional Guerbet reaction in which an alcohol having a large number of carbon atoms, i.e., 6 or more carbon atoms, is used as a starting material, the reactant has considerably reduced reaction activity when reacted in pressurized hydrogen, as described in *J. Mol. Catal.*, 1985, 33, p. 1. In contrast, in the reaction in which an alcohol having 4 or less carbon atoms, such as ethanol, is used as a starting material as in the invention, it is surprising that reaction activity improves rather than decreases despite the fact that the reaction is conducted in pressurized hydrogen. Although the partial hydrogen pressure in the reaction according to the invention is 0.1 MPa or higher, a preferred range of partial hydrogen pressure is from 0.5 MPa to 20 MPa. A more preferred range of partial hydrogen pressure is from 0.6 MPa to 15 MPa, and a most preferred range of partial hydrogen pressure is from 1.0 MPa to 10 MPa. The larger the value of partial hydrogen pressure, the more the selectivity to n-butanol improves. The smaller the value thereof, the more the process is advantageous from the standpoint of profitability. For example, lower partial hydrogen pressures reduce the cost of reactor construction and facilitate reactor maintenance. Meanwhile, the total pressure of the reaction system is determined by the sum of the vapor pressures of the ethanol, reaction intermediates, n-butanol, by-products, etc., which depend on reaction temperature, the vapor pressure of a solvent in the case where the solvent is used, the partial pressure of an inert gas, e.g., nitrogen, in the case where the gas is contained, etc. The total pressure is not particularly limited. However, unnecessarily elevating the internal pressure of the reactor should be avoided from the standpoints of profitability and safety.

It is preferred that the transition metals in the invention should be transition metals in Group 8 to Group 10 of the periodic table (according to IUPAC *Mukikagaku Meimei-hō*, revised edition (1998)). Examples thereof include iron, ruthenium, osmium, cobalt, rhodium, iridium, nickel, palladium, and platinum. Preferred for reasons of high activity in the reaction are ruthenium, rhodium, iridium, nickel, palladium, and platinum. More preferred are ruthenium and rhodium. Most preferred is ruthenium. Such transition metals may be used alone or in combination of two or more thereof.

When any of those metals is used as a complex for the dimerization reaction according to the invention, a compound containing the metal is usually employed. Examples of the metallic compound include one or more compounds selected from the group consisting of iron compounds, ruthenium compounds, osmium compounds, cobalt compounds, rhodium compounds, iridium compounds, nickel compounds, palladium compounds, and platinum compounds. Preferred of these for reasons of high activity in the reaction are ruthenium compounds, rhodium compounds, iridium compounds, nickel compounds, palladium compounds, and platinum compounds. More preferred are ruthenium compounds and rhodium compounds. Most preferred are ruthenium compounds.

Examples of specific forms of those metallic compounds include halogen compounds and inorganic salts such as sulfates and nitrates, and further include acetates, acetylacetonato compounds, alkene coordination compounds, amine coordination compounds, pyridine coordination compounds, carbon monoxide coordination compounds, phosphine coordination compounds, and phosphite coordination compounds.

Specifically, examples of the iron compounds include $Fe(OAc)_2$, $Fe(acac)_3$, $FeCl_2$, $FeCl_3$, and $Fe(NO_3)_3$. Examples of the ruthenium compounds include $RuCl_3$, $Ru_3(CO)_{12}$, $Ru(OAc)_3$, $Ru(acac)_3$, $[Ru(CO)_2(OAc)]_n$, $[RuCl_2(cod)]_n$, $[CpRuCl]_n$, $[Cp*RuCl]_4$, $RuHCl(PPh_3)_3$, $RuH(CO)(PPh_3)_3$, $RuCl_2(PPh_3)_3$, and $RuH_2(PPh_3)_4$. Examples of the osmium compounds include $OsCl_3$, $OsH_2Cl_6$, $Os_3(CO)_{12}$, and $Os(OAc)_3$. Examples of the cobalt compounds include $Co(OAc)_2$, $Co(acac)_2$, $CoBr_2$, and $Co(NO_3)_2$. Examples of the rhodium compounds include $RhCl_3$, $Rh(OAc)_3$, $[Rh(OAc)_2]_2$, $Rh(acac)(CO)_2$, $[Rh(OAc)(cod)]_2$, $[RhCl(cod)]_2$, $RhCl(PPh_3)_3$, $[Cp*RhCl_2]_2$, $RhH(CO)(PPh_3)_3$, and $Rh_4(CO)_{12}$. Examples of the iridium compounds include $IrCl_3$, $Ir(OAc)_3$, $Ir(acac)_3$, $Ir(cod)(acac)$, $IrH(CO)(PPh_3)_3$, $[Cp*IrCl_2]_2$, $[IrCl(cod)]_2$, and $Ir_4(CO)_{12}$. Examples of the nickel compounds include $NiCl_2$, $NiBr_2$, $Ni(NO_3)_2$, $NiSO_4$, $Ni(cod)_2$, $Ni(acac)_2$, $Ni(OAc)_2 \cdot 4H_2O$, $NiCl_2(Ph_2PCH_2CH_2PPh_2)$, and $NiCl_2(PPh_3)_3$. Examples of the palladium compounds include $Pd(0)$, $PdCl_2$, $PdBr_2$, $PdCl_2(cod)$, $PdCl_2(PPh_3)_2$, $Pd(PPh_3)_4$, $Pd_2(dba)_3$, $K_2PdCl_4$, $PdCl_2(CH_3CN)_2$, $Pd(dba)_2$, $Pd(NO_3)_2$, $Pd(OAc)_2$, $PdSO_4$, and $Pd(acac)_2$. Examples of the platinum compounds include $PtBr_2$, $PtCl_4$, $Pt(acac)_2$, $PtH_2(OH)_6$, $PtH_2Cl_6$, $PtCl_2(PPh_3)_2$, $PtCl_2(cod)$, $PtCl_2(CH_3CN)_2$, $PtCl_2(PhCN)_2$, $Pt(PPh_3)_4$, $K_2PtCl_4$, $Na_2PtCl_6$, and $H_2PtCl_6$. (In the formulae, cod represents 1,5-cyclooctadiene; dba represents dibenzylideneacetone; Ph represents a phenyl group; acac represents an acetylacetonato group; Ac represents an acetyl group; Cp represents a cyclopentadienyl group; and Cp* represents a pentamethylcyclopentadienyl group.)

In the invention, the forms of the metallic compounds described above are not particularly limited, and the compounds may be monomers, dimers, and/or polymers. When those metallic compounds are used, one specific metallic compound may be employed or a plurality of compounds of the same metal may be employed in combination. Alternatively, compounds of two or more different metals may be made to coexist.

Those metallic compounds may be used by themselves or may be used in the state of being supported on a support. In the case where a metallic compound is fixed to a support, use can be made, for example, of metal oxides such as zeolites, silica, alumina, silica-alumina, zirconia, magnesia, and titania, or of activated carbon, graphite, carbon nanotubes, or the like. The amount of the metallic compound to be fixed to such a support may be in the range of 0.01%-60%, preferably 0.1%-30%, more preferably 1%-20%, in terms of the weight of the metal itself based on the weight of the whole support. The larger the weight of the metal, the higher the activity of the catalyst and the greater the advantage that the amount itself of the catalyst to be used can be reduced. The smaller the weight of the metal, the lower the metal content in the catalyst and the greater the advantage that catalyst cost can be reduced.

The amount of those metallic compounds to be used is not particularly limited. However, from the standpoints of catalytic activity and profitability, the amount of the metallic compounds to be used is from $1 \times 10^{-6}$ (1 ppm by mole) to 1 mole-equivalent, preferably in the range of from $1 \times 10^{-5}$ (10 ppm by mole) to 0.1 mole-equivalent, especially preferably in the range of from $1 \times 10^{-4}$ (100 ppm by mole) to 0.01 mole-equivalent, to the amount of the ethanol as a starting material. The larger the use amount thereof, the more the catalytic activity improves. However, this case may result in an increase in catalyst cost. On the other hand, the smaller the use amount thereof, the lower the catalyst cost. However, this case may result in no increase in catalytic activity.

The ligands of the complex in the invention are not particularly limited. However, it is preferred to use either a ligand including as a coordinating atom a nitrogen atom coordinated to a transition metal, such as a ligand derived from an amine compound and/or a pyridine compound, or a ligand derived from a phosphine compound.

The amine or pyridine compound which can be used in the invention may be any of a unidentate amine, bidentate or multidentate ("multidentate" means terdentate or higher-order dentate; the same applies hereinafter) amine, unidentate pyridine, and bidentate or multidentate pyridine, and these compounds each may have substituents. In the case where two or more substituents are possessed, the substituents may be bonded to each other to form a cyclic structure.

The substituents which may be possessed by the amine compounds or the pyridine compounds are not particularly limited so long as the substituents do not lessen the effect of the invention. Examples thereof include alkyl groups, alkoxy groups, aryl groups, aryloxy groups, amino, cyano, ester groups, hydroxy, and halogen atoms. The alkyl groups include branched alkyl groups and cycloalkyl groups, and the aryl groups include heterocyclic aryl groups in each of which the ring is composed of one or more carbon atoms and one or more atoms of other element(s), e.g., nitrogen, oxygen, and sulfur. Usually, substituents having a molecular weight of about 200 or lower are used.

Specific examples of the amine compound include unidentate primary amines such as n-propylamine, n-octylamine, isopropylamine, 4-chlorobutylamine, aniline, and 4-methoxyaniline, unidentate secondary amines such as di-n-butylamine, di-n-octylamine, di-sec-butylamine, diphenylamine, methylphenylamine, and morpholine, unidentate tertiary amines such as triethylamine, tri-n-butylamine, tri-n-hexylamine, triphenylamine, ethylphenyl-n-propylamine, and tris (3-methoxy-propyl)amine, bidentate primary amines such as 1,4-diaminobutane, 1,6-diaminohexane, 2,2'-diamino-1,1'-binaphthyl, and 1,2-bis(diaminomethyl)benzene, bidentate secondary amines such as N,N'-dimethylethylenediamine, N,N'-dimethyl-1,3-propanediamine, N,N'-dimethyl-1,2-diaminobenzene, and piperazine, bidentate tertiary amines such as N,N,N',N'-tetramethyl ethylenediamine, N,N,N',N'-tetraethyl-ethylenediamine, N,N,N',N'-tetramethyl-1,4-butanediamine, 1,4-dimethyl piperazine, 2,2'-bis(dimethylamino)biphenyl, and N,N,N',N'-tetramethyl-1,2-phenylenediamine, and multidentate amine compounds such as 1,4,7-triazacyclononane, 1,4,8,11-tetramethyl-1,4,8,11-tetraazacyclotetradecane, and 1,1,4,7,7-pentamethyl-1,4,7-tri azaheptane.

Specific examples of the pyridine compound include unidentate pyridines such as pyridine, 2-methylpyridine, 3-methylpyridine, 4-methylpyridine, 2,3-dimethylpyridine, 2,4-dimethylpyridine, 2,5-dimethylpyridine, 2,6-dimethylpyridine, 4-methoxypyridine, 4-t-butylpyridine, 2-chloropyridine, quinoline, 2-methylquinoline, isoquinoline, 1-methylisoquinoline, and 5-azaphenanthrene, bidentate pyridines such as 2,2'-bipyridyl, 2,2'-biquinolyl, 1,8-diazabiphenylene, 1,10-phenanthroline, bis(2-pyridyl) methane, 1,2-bis(2-pyridyl)-1,2-ethanedione, 1,2-bis(2-pyridyl)ethane, and 1,2-bis(2-quinolyl)ethane, and multidentate pyridines such as 2,2':6',2''-terpyridyl, 4,4',4''-tri-t-butyl-2,2':6',2''-terpyridyl, 2,6-bis(di(2-pyridyl)methyl) pyridine, and 2,6-bis(8-quinolyl)pyridine. The pyridine compounds in the invention include polycyclic pyridine derivatives such as ones composed of a pyridine ring, such as quinoline or isoquinoline, and an aromatic ring fused thereto.

Preferred of those amine compounds or pyridine compounds are bidentate or multidentate tertiary amines or bidentate or multidentate pyridines. Especially preferred are 2,2'-bipyridyl or derivatives thereof. The reason for the preference is that the bidentate or multidentate amines or pyridines can more strongly coordinate to metals and the active species are apt to be maintained even under reaction conditions including a high reaction temperature, as in the reaction according to the invention. Specific examples thereof include 2,2'-bipyridyl, 2,2'-biquinolyl, 1,10-phenanthroline, 4,4'-dimethyl-2,2'-bipyridyl, 4,4'-dichloro-2,2'-bipyridyl, 2,9-dimethyl-1,10-phenanthroline, diethyl 2,2'-biquinoline-4,4'-dicarboxylate, and 5-nitro-1,10-phenanthroline.

The kind of the amine or pyridine compound and the amount of the compound to be used relative to the metal are not particularly limited so long as the compound does not exert an adverse influence on the reaction activity of the catalyst and on the reaction product (intermediates). However, the amount thereof is in the range of generally 0.1-10, 000, preferably 0.5-500, especially preferably 1.0-100, in terms of the molar proportion of the ligand to the metallic compound. When the value thereof is sufficiently large, there is scarcely any influence on the reaction even when the ligand decomposes to some degree during the reaction. However, the larger the use amount of the ligand, the more the process is economically disadvantageous accordingly. Conversely, the smaller the value thereof, the more the process is economically advantageous. However, care should be taken because ligand decomposition is apt to cause conversion of the catalyst to the metal, etc.

Those compounds may be supplied to the reaction system after having been complexed beforehand, or may be supplied as they are. Furthermore, one amine compound and/or one pyridine compound may be used to conduct the reaction, or two or more amine compounds or pyridine compounds may be simultaneously used to conduct the reaction.

Examples of the phosphine compound usable in the reaction according to the invention include trialkylphosphines, dialkylmonoarylphosphines, monoalkyl-diarylphosphines, and triarylphosphines. These compounds may have substituents. With respect to the mode of coordination to the transition metal, the phosphine compound may have any of unidentate, bidentate, and multidentate ("multidentate" means terdentate or higher-order dentate; the same applies hereinafter) structures. An explanation is added here on the alkyl groups or aryl groups bonded to the phosphorus atom in the phosphine compound. Each group may have substituents, and two or more groups may be bonded to each other to form a cyclic structure. In the case where the alkyl or aryl groups have substituents, examples of the substituents include alkyl groups, alkoxy groups, aryl groups, aryloxy groups, amino, cyano, ester groups, hydroxy, and halogen atoms. The alkyl groups include branched alkyl groups and cycloalkyl groups, and the aryl groups include heterocyclic aryl groups in each of which the ring is composed of one or more carbon atoms and one or more atoms of other element(s), e.g., nitrogen, oxygen, and sulfur. Usually, substituents having a molecular weight of about 200 or lower are used here.

Specific examples of the phosphine compound include unidentate trialkylphosphines such as trimethylphosphine, triethylphosphine, triisopropyl-phosphine, tri-t-butylphosphine, tri-n-octylphosphine, tribenzylphosphine, trineopentylphosphine, tricyclohexylphosphine, tris(2-chloroethyl) phosphine, and methyldi(n-octyl)phosphine, unidentate dialkylmonoarylphosphines such as dimethylphenylphosphine, di-n-butylphenylphosphine, di-n-octylphenylphosphine, dicyclohexylphenylphosphine, diisopropyl-2-pyridylphosphine, 2-(di-t-butyl-phosphino)biphenyl, bis(2-chloroethyl)-4-t-butylphenylphosphine, bis(3-hydroxy-propyl)-1-naphthylphosphine, and methylethylphenylphosphine, unidentate monoalkyldiarylphosphines such as methyldiphenylphosphine, n-butyl-diphenyl-phosphine, isopropyldiphenylphosphine, benzyldiphenylphosphine, cyclohexylbis(3-pyridyl)phosphine, t-butylbis(3-chlorophenyl)phosphine, and methylphenyl-2-naphthylphosphine, unidentate triarylphosphines such as triphenylphosphine, tris(2-naphthyl)phosphine, tris(4-fluorophenyl)phosphine, tris(4-chlorophenyl)phosphine, tris(4-bromophenyl)phosphine, tris(4-methoxyphenyl)phosphine, tris(2-methyl-phenyl)phosphine, 2-bromophenyldiphenylphosphine, diphenyl(pentafluorophenyl)-phosphine, diphenyl-2-pyridylphosphine, and 1-naphthyl-4-chlorophenyl-3-pyridylphosphine, bidentate trialkylphosphines such as 1,2-bis(dimethyl-phosphino)ethane, 1,3-bis(dimethylphosphino)propane, 1,2-bis(dicyclohexyl-phosphino)ethane, 1,5-bis(diethylphosphino)pentane, and 2,2'-bis(dibenzyl-phosphinomethyl)biphenyl, bidentate dialkylmonoarylphosphines such as 1,2-bis(diethylphosphino)benzene, 1,8-bis(dimethylphosphino)naphthalene, 2,2'-bis(dimethylphosphino)biphenyl, 9,9-dimethyl-4,5-bis(di-t-butylphosphino)-xanthene, bis(2-diethylphosphinophenyl)ether, and 1,5-bis(phenyl-methylphosphino)pentane, bidentate monoalkyldiarylphosphines such as 1,2-bis(diphenylphosphino)ethane, 1,3-bis(diphenylphosphino)propane, 1,4-bis(diphenyl-phosphino)butane, 1,5-bis(diphenylphosphino)pentane, 1,6-bis(diphenylphosphino)-hexane, 2,2'-bis(diphenylphosphinomethyl)biphenyl, and 2,2'-bis(phenylmethyl-phosphino)-1,1'-binaphthyl, and bidentate triarylphosphines such as 2,2'-bis(diphenylphosphino)biphenyl, 2,2'-bis(diphenylphosphino)-1,1'-binaphthyl, 1,2-bis(diphenylphosphino)benzene, 1,4-bis(diphenylphosphino)benzene, bis(2-biphenylphosphinophenyl)ether, and 9,9-dimethyl-4,5-bis(diphenylphosphino)-xanthene. These compounds may be used alone or in combination of two or more thereof. Preferred of those phosphine compounds from the standpoint of improving catalytic activity are trialkyl phosphines and triarylphosphines. In particular, tribenzylphosphine is preferred among the trialkylphosphines, and triphenylphosphine is preferred among the triarylphosphines. With respect to the mode of coordination of the phosphine compound as a ligand, unidentate and bidentate coordination is preferred among unidentate, bidentate, and multidentate coordination for reasons of improving catalytic activity and reducing ligand cost. Especially preferred is unidentate coordination.

The kind of the phosphine compound and the amount of the compound to be added relative to the metal are not particularly limited so long as the compound does not exert an adverse influence on the reactivity of the catalyst and on the reaction product (intermediates). However, the amount thereof is in the range of generally 0.1-10,000, preferably 0.5-500, especially preferably 1.0-100, in terms of the proportion (molar proportion) thereof to the metallic compound. When the value thereof is sufficiently large, an influence on the reaction can be made slight even when the ligand decomposes to some degree during the reaction. However, the larger the use amount of the ligand, the more the process is economically disadvantageous accordingly. Conversely, the smaller the value thereof, the more the process is economically advantageous. However, care should be taken because ligand decomposition is apt to cause conversion of the catalyst to the metal, etc.

With respect to methods of addition, a metallic compound and a phosphine compound may be separately added to the reaction system, or may be used in the form of a complex prepared beforehand. Furthermore, one phosphine compound only may be used to conduct the reaction, or two or more phosphine compounds may be simultaneously used to conduct the reaction.

Examples of the base usable in the invention include bases such as inorganic bases, organic bases, and Lewis bases. Specifically, examples of the inorganic bases include the hydroxides of alkali metals, such as LiOH, NaOH, KOH, and CsOH, carbonates of alkali metals, such as $Li_2CO_3$, $Na_2CO_3$, $K_2CO_3$, and $Cs_2CO_3$, hydrogen carbonates of alkali metals, such as $LiHCO_3$, $NaHCO_3$, $KHCO_3$, and $CsHCO_3$, hydroxides of alkaline earth metals, such as $Mg(OH)_2$, $Ca(OH)_2$, and $Ba(OH)_2$, and carbonates of alkaline earth metals, such as $MgCO_3$, $CaCO_3$, and $BaCO_3$. Examples of the organic bases include alkoxide compounds of alkali metals, such as methoxysodium, ethoxysodium, t-butoxysodium, methoxypotassium, ethoxypotassium, and t-butoxypotassium, carboxylates of alkali metals, such as sodium acetate, sodium butyrate, potassium acetate, and potassium butyrate, pyridine and pyridine derivatives such as 4-methylpyridine, tertiary amines such as triethylamine, triisopropylamine, tri-n-octylamine, and 1,5-diazabicyclo[2.2.2]octane, other amines including piperidine, N-methylpiperidine, and morpholine, cyclic amidine derivatives such as 1,8-diazabicyclo[5.4.0]undecene-7 (abbreviation: DBU) and 1,5-diazabicyclo-[4.3.0]nonene-5 (abbreviation: DBN), phosphazene bases such as t-butyl-iminotris(dimethylaminophospholane (abbreviation: $P_1$-t-Bu) and 1-t-butyl-4,4,4-tris(dimethylamino)-2,2-bis[tris(dimethylamino)phosphoranylideneamino]-2$\Lambda^5$,4$\Lambda^5$-catenadi (phosphazene) (abbreviation: $P_4$-t-Bu), and proazaphosphatolan bases such as 2,8,9-triisopropyl-2,5,8,9-tetraaza-1-phosphabicyclo[3.3.3]undecane and 2,8,9-trimethyl-2,5,8,9-tetraaza-1-phosphabicyclo[3.3.3]undecane.

Preferred of those bases are bases having relatively high basicity so as to be capable of causing the aldol condensation reaction to proceed. Preferred are the hydroxides of alkali metals, such as LiOH, NaOH, KOH, and CsOH, carbonates of alkali metals, such as $Li_2CO_3$, $Na_2CO_3$, $K_2CO_3$, and $Cs_2CO_3$, and alkoxide compounds of alkali metals, such as methoxysodium, ethoxysodium, t-butoxysodium, methoxypotassium, ethoxypotassium, and t-butoxypotassium.

The amount of the basic compound to be used varies depending on the kind of the metallic compound and reaction conditions. However, the amount thereof is in the range of generally 0.1-1,000, preferably 1-500, especially preferably 10-100, in terms of the proportion (molar proportion) thereof to the metallic compound. Those bases may be used alone, or may be used in combination of two or more thereof.

The reaction according to the invention is usually conducted in a liquid phase. The state of the liquid phase may be either a homogeneous system, or a state including separated multiple phases, or a slurry state.

In the invention, the starting material may be reacted in either the presence or the absence of a solvent.

When a solvent is to be used, preferred solvents are ones in which the catalyst, basic compound, and starting-material compound are at least partly soluble and which do not exert an adverse influence on reaction activity and reaction selectivity. Such solvents are usable without particular limitations. However, because the reaction according to the invention is conducted in the presence of a base, a solvent which is neutral or alkaline is usually used in order to maintain the effect of the base. Besides water, examples of the solvent include ethers such as diglyme (diethylene glycol dimethyl ether), triglyme (triethylene glycol dimethyl ether), diphenyl ether, dibenzyl ether, diallyl ether, tetrahydrofuran (THF), and dioxane, amides such as N-methyl-2-pyrrolidone, dimethylformamide, and N,N-dimethylacetamide, esters such as ethyl acetate, butyl acetate, ethyl butyrate, butyl butyrate, γ-butyrolactone, and di(n-octyl) phthalate, aromatic hydrocarbons such as benzene, toluene, xylene, ethylbenzene, and dodecylbenzene, aliphatic hydrocarbons such as pentane, hexane, heptane, octane, decane, and dodecane, halogenated hydrocarbons such as chloroform, dichloromethane, and carbon tetrachloride, and nitriles such as acetonitrile, propionitrile, and benzonitrile. Other examples include high-boiling compounds having a higher boiling point than ethanol and n-butanol, which are a starting material and a product, respectively.

The amount of those solvents to be used is not particularly limited. However, the amount thereof is generally 0.1-20 times, preferably 0.2-10 times, the weight of the starting-material alcohol. One of those solvents may be used alone, or two or more solvents may be used in combination.

In the case where the raw-material alcohol is ethanol, the atmosphere in the reaction system according to the invention includes the vapors of the raw-material ethanol, reaction intermediates, n-butanol, by-products, etc., and further includes the vapor of a solvent when the solvent is used. However, an inert gas such as nitrogen or argon may be present as another ingredient. An especially noteworthy point is that oxygen inclusion by air leakage into the system, etc. is causative of catalyst deterioration, in particular, oxidative disappearance of the phosphine compound, and it is therefore desirable to minimize the amount of oxygen present.

Reaction temperature is not particularly limited so long as a temperature at which the catalytic reaction proceeds is used. However, temperatures of 30-280° C. are preferred, and temperatures of 80-230° C. are more preferred. Most preferred are temperatures of 110-200° C.

With respect to the mode of reaction operation for carrying out the reaction according to the invention, any of continuous, semi-continuous, and batch processes can be conducted using a complete-mixing reactor of the stirring type or a plug flow type reactor.

For separating the dimeric alcohol obtained by the reaction from the metallic catalyst and the base, any of all separating operations used in ordinary liquid-catalyst recycling processes can be employed. Examples thereof include distillation operations such as simple distillation, vacuum distillation, thin-film distillation, and steam distillation and other separating operations including gas-liquid separation, liquid-liquid separation, evaporation, gas stripping, gas absorption, and extraction. These separating operations each may be conducted as independent steps, or two or more ingredients may be simultaneously separated. In the case where part of the starting-material ethanol and reaction intermediates, such as acetaldehyde and crotonaldehyde, remain unreacted, these compounds may be recovered by the same separating techniques and recycled to the reactor. This method renders the process more economical. It is also desirable from the standpoint of profitability that the catalyst and basic compound which have been separated should be recycled without undergoing any treatment or be recovered, reactivated, and then reused. In particular, when the reaction according to the invention has been conducted using ethanol as a starting material, the n-butanol yielded as a dimeric alcohol can further successively undergo the same reaction to thereby produce trimeric alcohols (hexanols), tetrameric alcohols (octanols), etc. as by-products in small amounts. Specifically, 2-ethylbutanol and n-hexanol are observed as trimeric-alcohol by-products, and 2-ethylhexanol, n-octanol, etc. are observed as tetrameric-alcohol by-products. In some cases, such compounds also may be separated, purified, and effectively utilized.

EXAMPLES

The invention will be explained below in more detail by reference to Examples. However, the invention can be variously modified unless the modifications depart from the spirit of the invention, and should not be construed as being limited to the following Examples.

Examples 1 to 6 and Comparative Example 1

Into a stainless-steel autoclave having a capacity of 50 mL were introduced 47.4 mg (0.119 mmol) of Ru(acac)$_3$, 187.3 mg (0.714 mmol) of triphenylphosphine, 266.0 mg (2.371 mmol) of t-butoxypotassium, 3.078 g (66.816 mmol) of ethanol, and 0.321 g (1.886 mmol) of n-dodecane as an internal reference for analysis by gas chromatography (GC), in a nitrogen atmosphere. Hydrogen gas having a given pressure was introduced thereinto at 20° C. Thereafter, the autoclave kept in a closed state was heated at 180° C. for 3 hours to react the mixture and then cooled to room temperature. After pressure release, the liquid reaction mixture was analyzed by GC. The operation described above was conducted using hydrogen gas pressures set at 0.2 MPa, 0.5 MPa, 1.0 MPa, 2.0 MPa, 3.0 MPa, and 4.0 MPa each as the given pressure, in Examples 1 to 6, respectively. The partial hydrogen pressures under the reaction conditions in Examples 1 to 6 were calculated at 0.3 MPa, 0.8 MPa, 1.5 MPa, 3.1 MPa, 4.6 MPa, and 6.2 MPa, respectively, while ignoring dissolution of the hydrogen gas in the liquid reaction mixture.

Furthermore, a reaction was conducted in the same manner as in Example 1, except that hydrogen gas was not introduced at all. This operation is referred to as Comparative Example 1. Incidentally, the yield of n-butanol and the selectivity to n-butanol can be determined using the following equations.

Yield of n-butanol (%)={[(amount of n-butanol yielded (mol))×2]/(amount of ethanol introduced (mol)}×100

Selectivity to n-butanol (%)=[(yield of n-butanol)/ (conversion of ethanol)]×100

The partial hydrogen pressures, the yields of n-butanol (NBA), and the selectivities thereto in Comparative Example 1 and Examples 1 to 6 are shown in Table 1. Graphs showing the yields of NBA and selectivities to NBA obtained with the partial hydrogen pressures during the reaction are given in FIG. 1, the graphs being drawn using the numerical values given in Table 1.

TABLE 1

|  | Partial hydrogen pressure* (MPa) | Yield of n-butanol (%) | Selectivity to n-butanol (%) |
|---|---|---|---|
| Comparative Example 1 | 0 | 7 | 25 |
| Example 1 | 0.3 | 10 | 26 |
| Example 2 | 0.8 | 16 | 58 |
| Example 3 | 1.5 | 17 | 64 |
| Example 4 | 3.1 | 20 | 92 |
| Example 5 | 4.6 | 17 | 92 |
| Example 6 | 6.2 | 17 | 95 |

*Estimated value of partial hydrogen pressure in the system during reaction

It can be seen from the results that when the reaction is conducted in pressurized hydrogen, the selectivity to the target dimeric alcohol (NBA) is greatly improved and the reaction yield under the same conditions is also improved.

Example 7

Into a stainless-steel autoclave having a capacity of 50 mL were introduced 229.0 mg (0.239 mmol) of $RuCl_2(PPh_3)_3$, 187.8 mg (0.716 mmol) of triphenylphosphine, 535.7 mg (4.774 mmol) of t-butoxypotassium, 6.307 g (136.905 mmol) of ethanol, 5.525 g (52.032 mmol) of o-xylene as a solvent, and 0.595 g (3.491 mmol) of n-dodecane as an internal reference for analysis by GC, in a nitrogen atmosphere. Hydrogen gas of 2.0 MPa was introduced at 20° C. Thereafter, the autoclave kept in a closed state was heated at 180° C. for 2 hours to react the mixture and then cooled to room temperature. After pressure release, the liquid reaction mixture was analyzed by GC. As a result, the yield of NBA was 21% and the selectivity to NBA was 93%.

Comparative Example 2

A reaction was conducted in the same manner as in Example 7, except that hydrogen gas was not introduced before the reaction. The resultant reaction mixture was analyzed by GC. As a result, the yield of NBA was 18% and the selectivity to NBA was 59%.

A comparison between Example 7 and Comparative Example 2 shows that when the ruthenium complex different from the ruthenium complex used in Examples 1 to 6 was used as a catalyst, the same effect was produced. Namely, it can be seen that the yield of NBA and the selectivity to NBA are improved when the reaction is conducted in pressurized hydrogen.

Example 8

Into a stainless-steel autoclave having a capacity of 50 mL were introduced 95.1 mg (0.361 mmol) of $RhCl_3 \cdot 3H_2O$, 568.2 mg (2.166 mmol) of triphenylphosphine, 810.3 mg (7.221 mmol) of t-butoxypotassium, 6.308 g (136.924 mmol) of ethanol, 5.492 g (51.722 mmol) of o-xylene as a solvent, and 0.599 g (3.517 mmol) of n-dodecane as an internal reference for analysis by GC, in a nitrogen atmosphere. Hydrogen gas of 2.0 MPa was introduced at 20° C. Thereafter, the autoclave kept in a closed state was heated at 180° C. for 1 hour to react the mixture and then cooled to room temperature. After pressure release, the liquid reaction mixture was analyzed by GC. As a result, the yield of NBA was 20% and the selectivity to NBA was 93%.

Comparative Example 3

A reaction was conducted in the same manner as in Example 8, except that hydrogen gas was not introduced before the reaction. The resultant reaction mixture was analyzed by GC. As a result, the yield of NBA was 18% and the selectivity to NBA was 72%.

A comparison between Example 8 and Comparative Example 3 shows that the same effect was produced also when the rhodium complex was used as a catalyst. Namely, it can be seen that the yield of NBA and the selectivity to NBA are improved when the reaction is conducted in pressurized hydrogen.

While the invention has been described in detail and with reference to specific embodiments thereof, it will be apparent to one skilled in the art that various changes and modifications can be made therein without departing from the spirit and scope thereof.

This application is based on a Japanese patent application filed on Dec. 20, 2007 (Application No. 2007-329066), the contents thereof being herein incorporated by reference.

INDUSTRIAL APPLICABILITY

According to the invention, n-butanol can be highly efficiently produced as a dimeric alcohol with high selectivity through a reaction in which ethanol as a starting material is dimerized in the presence of a base and a transition metal complex. Consequently, the invention has a remarkable industrial value.

The invention claimed is:

1. A process of producing an alcohol, the process comprises dimerizing a starting-material alcohol having 4 or less carbon atoms in an environment having a partial hydrogen pressure of 0.5-20 MPa to form a dimeric alcohol, wherein the dimerization is conducted in the presence of a base, a complex comprising a transition metal, and a ligand derived from a phosphine compound.

2. The process claim 1, wherein the phosphine compound is a triarylphosphine.

3. The process of claim 1, wherein the transition metal is in Group 8 to Group 10.

4. The process of claim 3, wherein the transition metal in Group 8 to Group 10 is at least one selected from the group consisting of ruthenium, rhodium, iridium, nickel, palladium, and platinum.

5. The process of claim 1, wherein the starting-material alcohol having 4 or less carbon atoms is ethanol.

6. The process of claim 1, wherein the dimeric alcohol is formed with a yield equal to or greater than 15%, based on an amount of starting-material alcohol introduced, and with a selectivity equal to or greater than 50%, based on a conversion of the starting-material alcohol.

7. The process of claim 5, wherein the dimeric alcohol is formed with a yield equal to or greater than 15%, based on an amount of the ethanol introduced, and with a selectivity equal to or greater than 50%, based on a conversion of the ethanol.

8. The process of claim 1, wherein the dimeric alcohol is formed with a yield equal to or greater than 20%, based on an amount of starting-material alcohol introduced, and with a selectivity equal to or greater than 90%, based on a conversion of the starting-material alcohol.

9. The process of claim 5, wherein the dimeric alcohol is formed with a yield equal to or greater than 20%, based on an amount of the ethanol introduced, and with a selectivity equal to or greater than 90%, based on a conversion of the ethanol.

10. The process of claim 4, wherein the transition metal in Group 8 to Group 10 is at least ruthenium.

11. The process of claim 1, wherein the base is at least one selected from the group consisting of a hydroxide of an alkali metal, a carbonate of an alkali metal and an alkoxide of an alkali metal.

* * * * *